(12) United States Patent
Paddock et al.

(10) Patent No.: US 6,482,203 B2
(45) Date of Patent: Nov. 19, 2002

(54) DEFLECTABLE INTERSTITIAL ABLATION DEVICE

(75) Inventors: Kimberly A. Paddock, Newton, MA (US); James E. Mayberry, Franklin, MA (US); Charles D. Lennox, Hudson, NH (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/004,759

(22) Filed: Dec. 4, 2001

(65) Prior Publication Data

US 2002/0040221 A1 Apr. 4, 2002

Related U.S. Application Data

(63) Continuation of application No. 09/661,835, filed on Sep. 14, 2000, now Pat. No. 6,352,534, which is a continuation of application No. 08/940,519, filed on Sep. 30, 1977, now Pat. No. 6,238,389.

(51) Int. Cl.$^7$ ............................................. A61B 18/18
(52) U.S. Cl. ........................ 606/41; 606/46; 607/102; 600/146
(58) Field of Search .................... 607/101–112, 99; 606/41–52, 32, 34; 604/35; 600/146

(56) References Cited

U.S. PATENT DOCUMENTS

| 4,402,310 A | 9/1983 | Kimura ........................ 604/30 |
| 4,565,200 A | 1/1986 | Cosman ........................ 128/642 |
| 4,699,463 A | 10/1987 | D'Amelio et al. ........ 350/96.26 |
| 4,745,908 A | 5/1988 | Wardle ........................ 128/6 |
| 4,748,969 A | 6/1988 | Wardle ........................ 128/4 |
| 4,765,331 A | 8/1988 | Petruzzi et al. ........ 128/303.14 |

(List continued on next page.)

FOREIGN PATENT DOCUMENTS

| EP | 0 629 382 | 12/1994 |
| WO | WO 94/17856 | 8/1994 |
| WO | WO 95/10981 | 4/1995 |
| WO | WO 96/11638 | 4/1996 |
| WO | WO 96/26675 | 9/1996 |
| WO | WO 97/00049 | 1/1997 |
| WO | WO 97/13452 | 4/1997 |
| WO | WO 97/17027 | 5/1997 |
| WO | WO 97/17028 | 5/1997 |
| WO | WO 97/33524 | 9/1997 |

OTHER PUBLICATIONS

International Search Report for PCT/US98/20099.

*Primary Examiner*—Linda C. M. Dvorak
*Assistant Examiner*—David M. Ruddy
(74) *Attorney, Agent, or Firm*—Testa, Hurwitz & Thibeault, LLP (57) ABSTRACT

A deflectable interstitial ablation device includes an elongated housing, an electrode mounted within the elongated housing, a driver coupled to the electrode, an imaging device integrally mounted within the elongated housing and a deflection system disposed within the elongated housing. The elongated housing has a proximal end, a distal end, and a deflectable segment. The electrode is deployable from a first position within the elongated housing to a second position a predetermined distance beyond the distal end of the elongated housing. The electrode further has a flexible portion capable of deflecting with the deflectable segment of the elongated housing, and can be deployed by the driver with a sufficient force such that penetration of the urethral wall occurs in a single motion. The imaging device further has a flexible portion capable of deflecting with the deflectable segment of the elongated housing. The deflection system has a proximal end in communication with a steering mechanism, for controllably deflecting the deflectable segment of the elongated housing by any angle. The deflection of the deflectable segment allows deflection of the electrode and the imaging device, thus facilitating proper placement of the electrode.

18 Claims, 6 Drawing Sheets

U.S. PATENT DOCUMENTS

| | | | |
|---|---|---|---|
| 4,770,654 A | 9/1988 | Rogers et al. | 604/22 |
| 4,776,840 A | 10/1988 | Freitas et al. | 604/33 |
| 4,823,791 A | 4/1989 | D'Ameli et al. | 123/303.14 |
| 4,911,148 A | 3/1990 | Sosnowski et al. | 128/6 |
| 4,917,082 A | 4/1990 | Grossi et al. | 606/46 |
| 4,917,100 A | 4/1990 | Nottke | 128/749 |
| 4,936,842 A | 6/1990 | D'Amelio | 606/42 |
| 5,007,908 A | 4/1991 | Rydell | 606/47 |
| 5,069,223 A | 12/1991 | McRae | 128/734 |
| 5,091,656 A | 2/1992 | Gahn | 307/119 |
| 5,186,714 A | 2/1993 | Boudreault et al. | 604/21 |
| 5,195,958 A | 3/1993 | Phillips | 604/33 |
| 5,197,963 A | 3/1993 | Parins | 606/46 |
| 5,199,417 A | 4/1993 | Muller et al. | 128/6 |
| 5,273,535 A | 12/1993 | Edwards et al. | 604/95 |
| 5,281,218 A | 1/1994 | Imran | 606/41 |
| 5,370,675 A | 12/1994 | Edwards et al. | 607/101 |
| 5,403,311 A | 4/1995 | Abele et al. | 606/49 |
| 5,409,453 A * | 4/1995 | Lundquist et al. | 607/99 |
| 5,423,808 A | 6/1995 | Edwards et al. | 606/34 |
| 5,431,645 A * | 7/1995 | Smith et al. | 606/46 |
| 5,435,805 A | 7/1995 | Edwards et al. | 604/22 |
| 5,458,597 A | 10/1995 | Edwards et al. | 606/41 |
| 5,486,161 A | 1/1996 | Lax et al. | 604/22 |
| 5,527,331 A | 6/1996 | Kresch et al. | 606/170 |
| 5,549,644 A | 8/1996 | Lundquist et al. | 604/22 |
| 5,562,703 A | 10/1996 | Desai | 606/210 |
| 5,582,589 A | 12/1996 | Edwards et al. | 604/22 |
| 5,595,185 A | 1/1997 | Erlich | 128/754 |
| 5,599,346 A | 2/1997 | Edwards et al. | 606/41 |
| 5,667,488 A | 9/1997 | Lundquist et al. | 604/22 |
| 5,720,719 A | 2/1998 | Edwards et al. | 604/22 |
| 5,849,011 A | 12/1998 | Jones et al. | 606/47 |
| 5,871,481 A * | 2/1999 | Kannenberg et al. | 606/41 |
| 5,919,191 A | 7/1999 | Lennox et al. | 606/48 |

* cited by examiner

DEFLECTABLE INTERSTITIAL ABLATION DEVICE

This application is a continuation of U.S. patent application Ser. No. 09/661,835, filed on Sep. 14, 2000, which is a continuation of U.S. patent application Ser. No. 08/940,519, filed on Sep. 30, 1997, now U.S. Pat. No. 6,238,389. The disclosures of each of the above applications are incorporated by reference in their entirety herein.

BACKGROUND

Ablation devices can be used to treat tumors in the body. In particular, ablation devices can be used to treat benign prostatic hypertrophy or hyperplasia (BPH), a condition resulting in an enlargement of the prostate gland. This is a common medical problem typically experienced by men over 50 years of age. Hyperplastic enlargement of the prostate gland often leads to compression of the urethra, which results in obstruction of the urinary tract. An ablating needle can be used with a cystoscope to treat BPH by ablating a prostatic adenoma, which is a benign tumor inside the prostate. To perform the ablation procedure, a physician inserts a distal end of the cystoscope into the urethra of a patient while viewing the advance through an eye piece of the cystoscope. The needle electrode is also introduced into the urethra through a working channel of the cystoscope. The cystoscope and the needle electrode are typically introduced inside the urethra sequentially. The distal end of the needle electrode is positioned adjacent the prostate near the prostatic adenoma. The physician then causes the needle electrode to penetrate the urethral wall, such that it is positioned inside the prostatic adenoma. Radiofrequency (RF) energy is applied to the needle electrode to coagulate tissue surrounding the electrode. Coagulation causes necrosis of the prostatic adenoma, resulting in atrophy of the prostate and a reduction in the compressive forces that interfere with urine flow through the urethra.

During the ablation procedure, it is important that the needle electrode be positioned precisely, because inaccurate electrode placement can cause incontinence in the patient. Visualization is typically provided by inserting the needle electrode through a cystoscope. One disadvantage of the ablation device insertable through a cystoscope is that it is difficult to feed the device through a working channel of the cystoscope and requires a lot of juggling which can make accurate placement of the needle electrode difficult. Moreover, it is often difficult to observe the distal tip of the needle electrode as the electrode penetrates the urethral wall, because the distal end of the electrode is typically deflected in order to penetrate the urethral wall while the viewing device itself does not deflect along with the needle electrode.

Existing interstitial ablation systems are also uncomfortable for the patients and cumbersome for the physician performing the procedure. Most cystoscopes and ablation systems integrating imaging devices tend to be rigid and uncomfortable for patients when inserted through a body lumen such as the urethra. The systems also have numerous knobs and dials that the physician must adjust for controlling needle deployment, fluid introduction, and application of RF energy.

Thus, there remains a need for an interstitial ablation device that provides accurate electrode placement and better control of the electrode, reduces patient discomfort and simplifies the process of performing ablation.

SUMMARY OF THE INVENTION

In one aspect, the invention features a deflectable interstitial ablation device. In one embodiment, the device includes an elongated housing, an electrode mounted within the elongated housing, a driver coupled to the electrode, an imaging device integrally mounted within the elongated housing, and a deflection system disposed within the elongated housing. The elongated housing has a proximal end, a distal end, and a deflectable segment. The electrode is deployable from a first position within the elongated housing to a second position a predetermined distance beyond the distal end of the elongated housing, and has a flexible portion capable of deflecting with the deflectable segment of the elongated housing. The driver exerts a force sufficient to drive the electrode from the first position to the second position in a single motion. The imaging device has a flexible portion capable of deflecting with the deflectable segment of the elongated housing. The deflection system controllably deflects the deflectable segment of the elongated housing to a desired angle. The deflection system has a proximal end in communication with a steering mechanism.

In one embodiment, the imaging device includes a plurality of illumination optical fibers and a plurality of viewing optical fibers extending from the proximal end to the distal end of the elongated housing. The viewing optical fibers can comprise a fused bundle of viewing optical fibers surrounded by illumination optical fibers, wherein the viewing optical fibers are in communication with a lens disposed at the distal end of the elongated housing. In another embodiment, the electrode is a hollow needle electrode and an insulation sheath surrounds the needle electrode. The needle electrode and the insulation sheath are individually and slidably mounted inside the elongated housing, such that the insulation sheath is capable of covering a proximal portion of the needle electrode which extends beyond the distal end of the elongated housing. In still another embodiment, the driver coupled to the electrode can exert a force within the range of ¼ lb to 1 lb to drive the electrode from the first position to the second position in a single motion.

In another embodiment, the device includes an elongated housing, an electrode mounted within the elongated housing, an imaging device integrally mounted with the elongated housing, a deflection system disposed within the elongated housing, and a foot pedal for deploying the electrode.

In another aspect, the invention features a method for treating tissue. A deflectable interstitial ablation device is inserted into a body lumen which provides access to the tissue to be treated. The deflectable interstitial ablation device includes an elongated housing having a deflectable segment, a deployable electrode mounted within the elongated housing, a driver coupled to the electrode for exerting a force to drive the electrode, an imaging device integrally mounted with the elongated housing, and a deflection system disposed within the elongated housing. The distal end of the elongated housing is positioned near the tissue. The deflectable segment of the elongated housing is deflected toward the tissue, thereby deflecting the electrode and the imaging device toward the tissue along with the deflectable segment. The electrode is deployed to penetrate a wall of the lumen and to position a distal end of the electrode adjacent the tissue. Radio frequency energy is applied to the electrode in an amount and for a duration sufficient to ablate the tissue.

In one embodiment, an insulation sheath is deployed to cover a proximal portion of the deployed electrode to protect the wall of the lumen from directly contacting the needle electrode during the treatment. In another embodiment, a balloon disposed on a body of the elongated housing of the deflectable interstitial ablation device is inflated to secure the position of the elongated housing inside the lumen. In yet another embodiment, a basket disposed on a body of the elongated housing of the deflectable interstitial ablation device is expanded to secure a position. In still another embodiment, the distal end of the elongated housing is connected to an actuator in communication with a foot pedal and the foot pedal is depressed to deploy the electrode.

BRIEF DESCRIPTION OF THE DRAWINGS

The invention is described with particularity in the appended claims. The above and further advantages of this invention may be better understood by referring to the following description taken in conjunction with the accompanying drawings.

DETAILED DESCRIPTION

Figures 1A, 1B:
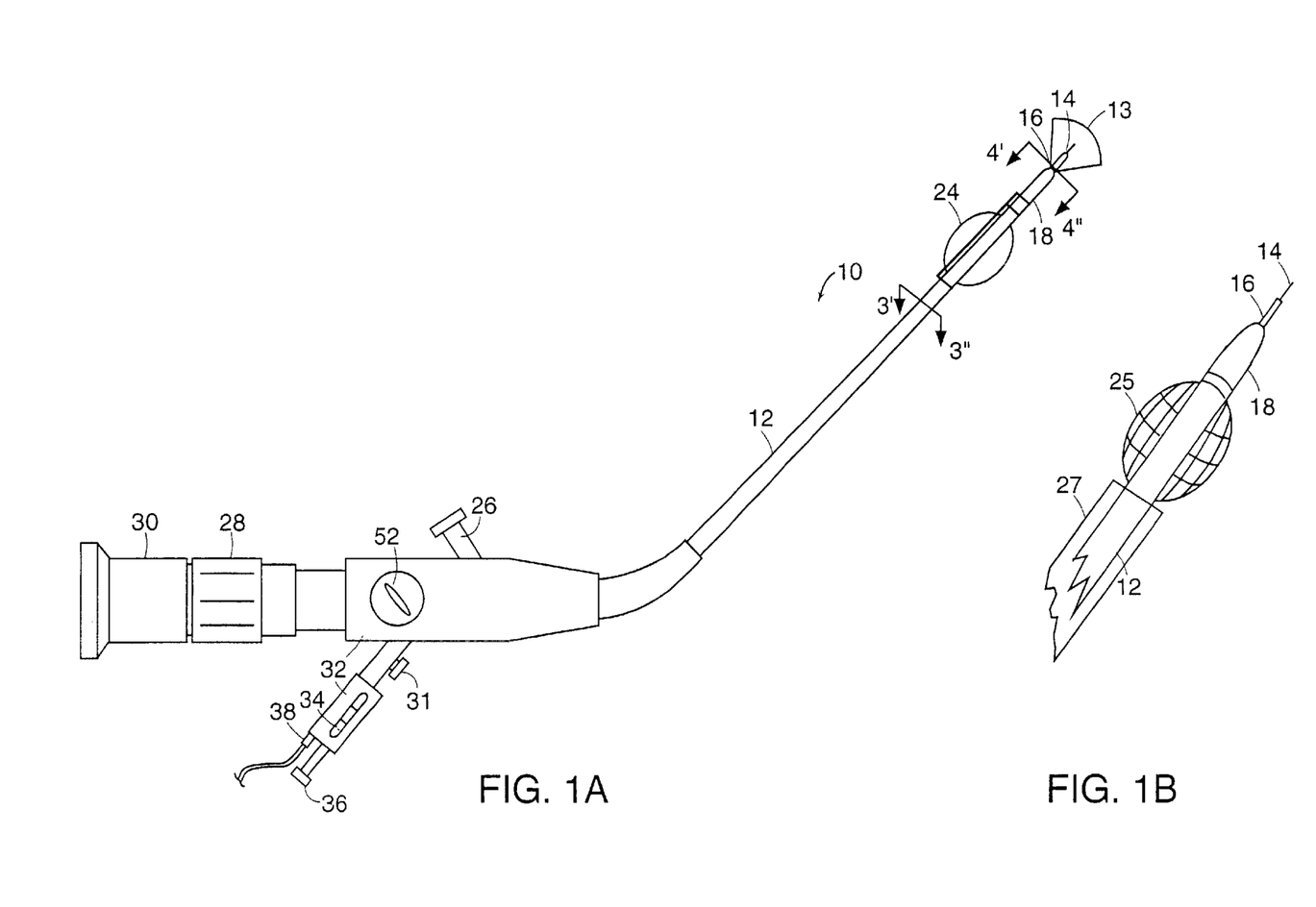
FIG. 1A shows a side view of a deflectable interstitial ablation device according to one embodiment of the invention.
FIG. 1B shows a portion of the deflectable interstitial ablation device having a basket for maintaining the placement of the device in a body lumen, according to one embodiment of the invention.
Figure 4:
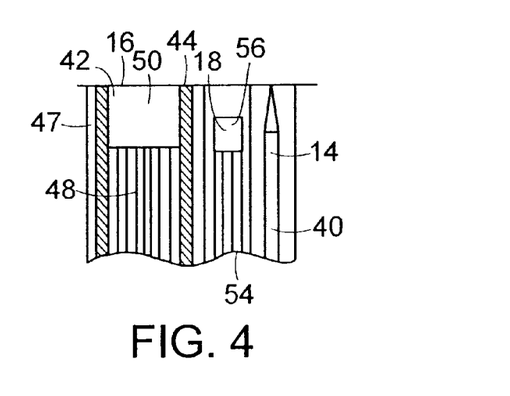
FIG. 4 shows a cross sectional view of a distal end of the deflectable interstitial ablation device of FIG. 1A cut through lines 4'–4".

Referring to FIGS. 1A and 4, a deflectable interstitial ablation device 10 includes an elongated housing 12, an electrode 14 extending within the elongated housing 12, an imaging device 16 integrally mounted with the elongated housing 12 and a deflection system 18 disposed within the elongated housing 12. The electrode 14 can comprise a needle electrode having a sharpened tip, or an electrode having a blunt tip. The elongated housing 12 has a proximal end, a distal end and a deflectable segment 22 further as further shown in FIG. 2. The elongated housing 12 can be constructed to be flexible so that the housing 12 may be inserted into the urethra without much discomfort. In one embodiment, the housing 12, can be, for example, a flexible multi-lumen catheter. In another embodiment, the housing 12, can be, for example, a substantially rigid, single lumen catheter having a deflectable segment 22. In one detailed embodiment, the housing 12 can have a diameter from about 15 to 16 French. It is to be appreciated that the diameter of the housing 12 can vary depending on the intended use of the ablation device 10.

In order to provide accurate placement of the electrode 14 inside the urethra, the present invention further provides means for stabilizing the position of the device 10 before deploying the electrode 14. In one embodiment, the elongated housing 12 of the invention includes a balloon 24 for securing the position of the device 10 while the electrode 14 is deployed at the ablation site. The elongated housing 12 includes a fluid port with a luer fitting 26 for introducing a fluid such as, for example, air or water for inflating the balloon 24. The fluid enters the balloon 24 through an inflation sleeve further shown in FIG. 2 to inflate the balloon 24. Another advantage provided by the balloon 24 is that the balloon 24 can block the blood vessels on the urethral wall and slow down heat conduction provided by the blood vessels. In one embodiment, the balloon 24 is compliant enough to fit inside the urethra. In one detailed embodiment, the balloon is constructed of latex or silicone. The diameter of the inflated balloon, in one embodiment, can be about 30 French.

In another embodiment, as shown in FIG. 1B, the elongated housing 12 can include a basket 25 to stabilize the device 10 position during deployment of the electrode 14. The basket 25 can comprise a wire mesh attached to an outer surface of the housing 12 surrounding the electrode 14, the imaging device 16 and the deflection system 18. The housing 12 can further be surrounded by an elongated sheath or catheter 27 such that the wire mesh comprising the basket 25 remains retracted during placement of the device and expands into the basket 25 shown in FIG. 1B to secure the position and placement of the electrode 14 after the electrode 14 has been exposed.

As shown, the proximal end of the elongated body 12 is in communication with a detachable eye piece coupler 28. A detachable eye piece 30 is coupled to the eye piece coupler 28, and the physician observes insertion of the device 10 into the urethra and the electrode 14 deployment by looking into the eye piece 30.

The proximal end of the elongated body 12 is also in communication with a handle 32. The handle 32 includes a slide member 34 for controlling deployment of the electrode 14. In one embodiment, the handle 32 can include two slide members (not shown), one for controlling the movement of the electrode 14 and the other for controlling the movement of the insulation sheath 40. In another embodiment, the slide member 34 can control the movement of the electrode 14 and the insulation sheath 40 secured to the electrode 14, to expose a predetermined amount of the electrode 14. As shown, the handle 32 also includes an electrical connector 38 for coupling the proximal end of the electrode 14 to a power source (not shown). In a preferred embodiment, the power source is an RF generator, however it is to be appreciated that other energy sources can be used, such as a microwave generator. The handle 32 further includes a luer port 36 for injecting fluid and an irrigation port 31 for removing fluid. In one embodiment, the fluid can be a conductive fluid for improving ablation procedures. Conductive fluids, can include, for example, saline and lydocaine. The use of a conducting fluid prevents desiccation of tissue and prevents an increase in the impedance during the ablation procedure.

Figure 2:
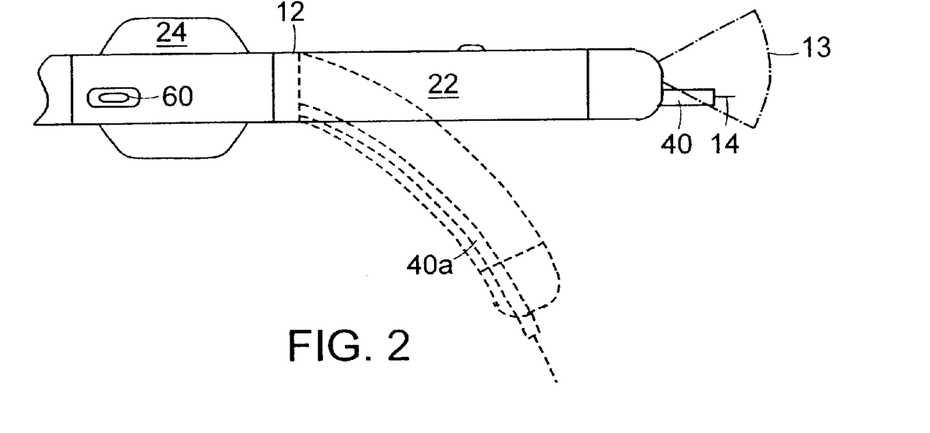
FIG. 2 illustrates a deflecting segment of the deflectable interstitial ablation device of FIG. 1A.

Referring to FIG. 2, the electrode 14 can be deployable from a first position within the elongated housing 12 to a second position beyond the distal end of the elongated housing 12 as shown. In one embodiment, the electrode 14 deploys to a predetermined distance beyond the distal end of the elongated housing 12. It is to be appreciated that the distance the electrode 14 deploys can vary depending on the intended application. As shown, the electrode 14 also has a flexible portion 40a which deflects along with the deflectable segment 22 of the elongated housing 12. In one detailed embodiment, the deflectable segment 22 is located at the distal end of the elongated housing 12 and has a dimension of from about 2.5 cm to about 4.5 cm measured from the distal end of the housing 12. It is to be appreciated that the length of the deflectable segment 22 can fall outside of the above range, depending on the intended application of the device 10. In one embodiment, the dimension and position of the flexible portion 40a of the electrode 14 corresponds to that of the deflectable segment 22 of the elongated housing 12. Referring to FIG. 2, illustrated in phantom in a deflected position, is the deflectable segment 22 and electrode's flexible portion 40a at the distal tip of the elongated housing 12.

Figure 3:
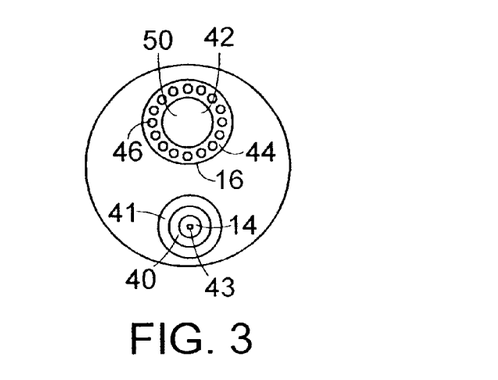
FIG. 3 shows a cross sectional view of the deflectable interstitial ablation device of FIG. 1A cut through lines 3'–3".

Referring to FIGS. 2 and 3, the electrode 14 can be a needle electrode surrounded by an insulation sheath 40. The needle electrode 14 and the insulation sheath 40 are placed inside an electrode guide tube 41 disposed inside the elongated housing 12. The insulation sheath 40, for example, may be constructed from an insulating polymer material such as polyimide. In another embodiment, the needle electrode 14 can be coated with an insulator, such as Teflon or ceramic. The needle electrode 14 and the insulation sheath 40 can be individually and slidably mounted inside the elongated housing 12, such that the insulation sheath 40 is capable of covering a proximal portion of the needle electrode 14 extending beyond the distal end of the elongated housing 12. By adjustably covering a proximal portion of the electrode 14 with the insulation sheath 40, the physician can control the amount of electrode 14 that is exposed, and thus control the conductive region and consequently, the size of the ablation area. This feature is important in transurethral interstitial ablation of prostate tissue, because urethral walls can be protected from being ablated during the procedure. Alternatively, the insulation sheath 40 can be fixed to a proximal portion of the needle electrode 14 and the needle electrode 14 can be slidably mounted inside the elongated housing 12. In another embodiment, as shown in FIG. 3, the electrode 14 can comprise a hollow electrode 14 including a passageway 43. In one embodiment, the hollow electrode 14 has an inner diameter of approximately 0.011 inches and an outer diameter of approximately 0.02 inches. The insulation sheath 40 has an outer diameter of approximately 0.03 inches and an inner diameter of about 0.025 inches. The electrode guide tube 41 has an inner diameter of about 0.039 inches. It is to be appreciated that the above dimensions are illustrative, and are not intended to be restrictive, as other dimensions can be used depending in whole or in part, on the intended application of the device.

Referring to FIGS. 3 and 4, the imaging device 16 disposed inside the elongated housing 12 includes a illumination region 44 and a viewing region 42. Both regions 42 and 44 can include a plurality of optical fibers 46 extending from the proximal end to the distal end of the elongated housing 12. In the embodiment of FIGS. 3 and 4, the illumination region 44 includes a plurality of optical fibers 46 in communication with a light source (not shown) at a proximal end. The plurality of optical fibers 46 surrounds the viewing region 42. The viewing region 42 can include a fused bundle of optical fibers 48 in communication with an objective lens 50 at the distal end for focusing an image. An example of the objective lens 50 is a gradient index (GRIN-self) objective lens having a diameter of about 0.039 inches. The illumination region 44 and the viewing region 42 may be arranged in other ways and may comprise optical components other than or in addition to those described above. In other embodiments, other imaging devices can be used for viewing the area of tissue in question. In one embodiment, the imaging device 16 is surrounded by an outer sheath comprising a polymeric material 47. In another embodiment, the imaging device 16 is disposed inside the elongated housing 12 without an outer sheath. In one detailed embodiment, the imaging device 16 has a viewing angle 13 of about 70 degrees, as shown in FIGS. 1 and 2. It is to be appreciated that the viewing angle 13 can be greater or less than 70 degrees depending in whole or in part, on the intended application of the device.

Referring to FIGS. 1 and 4, the deflection system 18 controllably deflects the deflectable segment 22 by an angle of up to 180 degrees in one direction and 180 degrees in the opposite direction with respect to the longitudinal axis of the elongated housing 12. In one embodiment, the deflection system 18 includes a flexible wire 54 extending from the proximal end to the distal end of the elongated housing 12 and a flat spring 56 in communication with the flexible wire 54 disposed at the distal end of the elongated housing 12. The proximal end of the flexible wire 54 is in communication with a steering mechanism 52, shown in FIG. 1A as mounted on the handle 32. The steering mechanism 52 can pull the flexible wire 54 and cause the flat spring 56 to gradually deflect toward a direction to which the wire 54 is pulled. Details of the steering mechanism are described in U.S. Pat. No. 5,273,535, which is incorporated herein by reference. In one detailed embodiment, the deflection system 18 has an outer diameter of approximately 0.02 inches. It is to be appreciated that the diameter of the deflection system 18 can vary depending in whole or in part, on the intended application of the device.

Referring to FIGS. 5A–5E, in another embodiment, the deflectable interstitial ablation device 10 further includes a driver 75 located in the handle 32 and coupled to the electrode 14 for kinetically deploying the electrode 14. In this embodiment, the electrode 14 can be a needle electrode having a sharpened tip. The driver 75 exerts a force sufficient to deploy the electrode 14 from inside the elongated housing 12 to a position beyond the distal end of the elongated housing 12 in a single motion. In one embodiment, the force of deployment can range from about ¼ lb to about 1 lb. A force in this range is sufficient to cause the electrode 14 to penetrate the urethral wall in a single motion. Kinetic deployment which permits sudden and high speed deployment facilitates electrode penetration through the urethral wall, reducing patient discomfort and improving the accuracy and control of needle deployment. In the present embodiment, such kinetic deployment is achieved by employing a driver 75 comprising a spring-operated actuating mechanism.

Figure 5A:
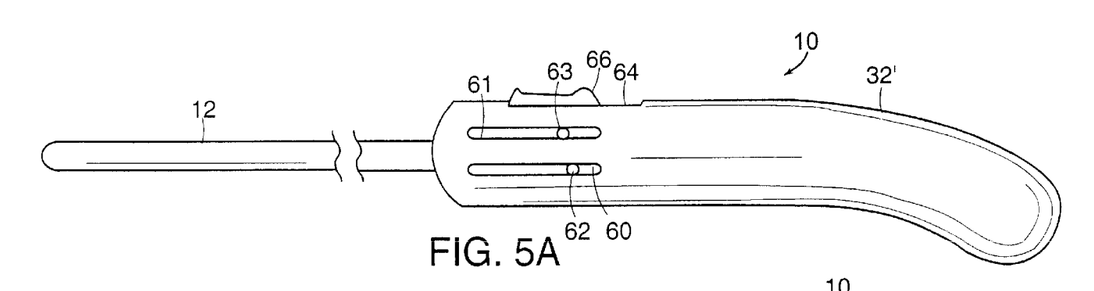
FIG. 5A is a side view of a kinetically deployable needle electrode according to one embodiment of the invention.
Figure 5B:
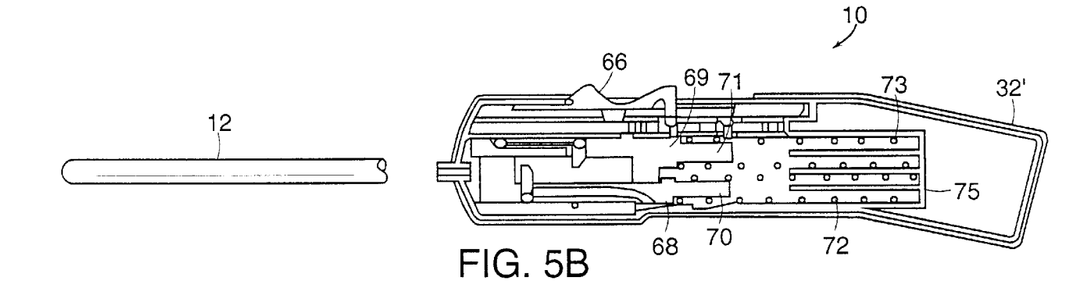
FIG. 5B is a cross sectional view of the kinetically deployable needle electrode of FIG. 5A prior to deployment.

Referring to FIG. 5A, the handle 32' includes slots 60 and 61 having levers 62 and 63, respectively, and a recess 64 having an actuator 66 on an outer surface of the handle 32'. Referring to FIGS. 5B to 5E, contained within the housing 32' are slide members 68 and 69. The slide member 68 is connected to the insulation sheath 40, and the slide member 69 is connected to the electrode 14. The lever 62 is connected to the slide member 68 and the lever 63 is connected to the slide member 69. Reduced proximal sections 70 and 71 of the slide members 68 and 69 are received within spring coils 72 and 73, respectively. The actuator 66 is operatively coupled to the slide member 69. In this embodiment, the electrode 14 and the insulation sheath 40 are sequentially propelled.

Figure 5C:
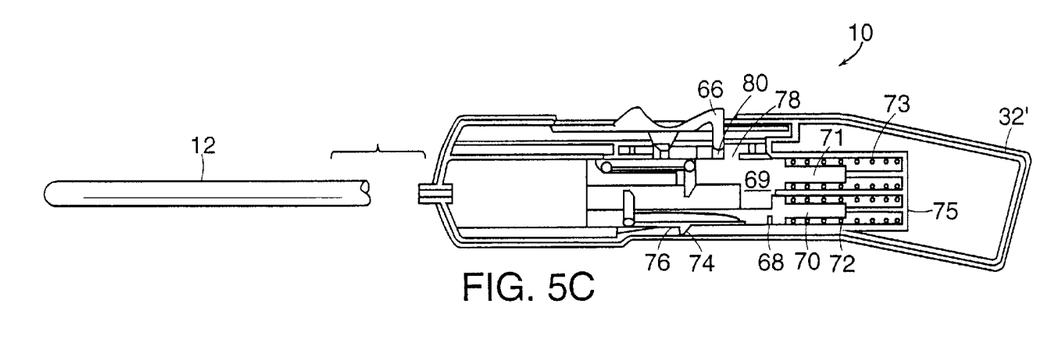
FIG. 5C is a cross sectional view of the kinetically deployable needle electrode of FIG. 5A in a loaded position.

Referring to FIG. 5C, prior to inserting the elongated sheath 12 inside the body, the device 10 is loaded by pulling the levers 62 and 63 in the proximal direction. As the lever 62 is pulled in the proximal direction, a projection 74 on the slide member 68 slides over and catches the distal surface of a catch or stop 76, and as the lever 63 is pulled, a projection 78 of the slide member 69 catches on a stop 80. Once the elongated sheath 12 is properly placed inside the body and the deflectable segment 22 is deflected by a desired angle, the needle electrode 14 and the insulation sheath 40 are deployed by pulling the actuator 66 proximally and then down.

Figure 5D:
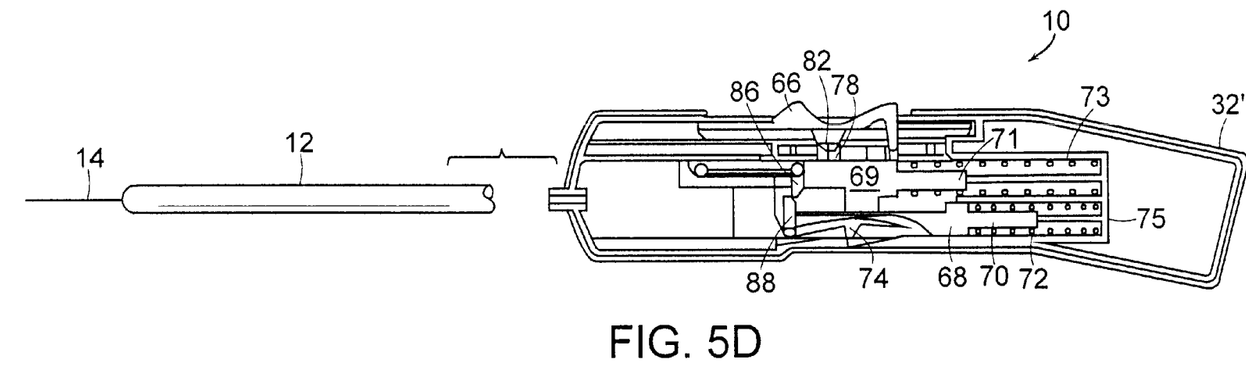
FIG. 5D is a cross sectional view of the kinetically deployable needle electrode of FIG. 5A with the needle electrode deployed.
Figure 5E:
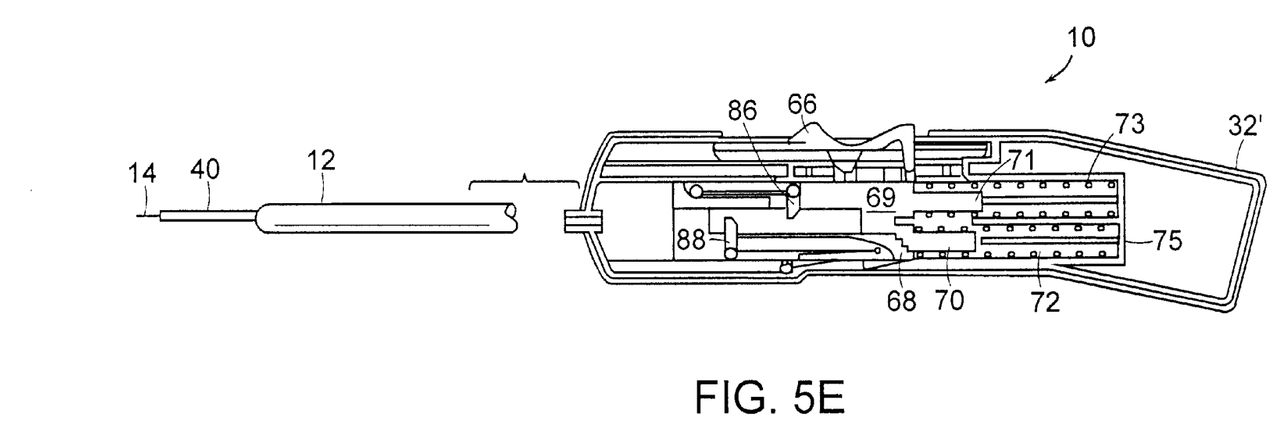
FIG. 5E is a cross sectional view of the kinetically deployable needle electrode of FIG. 5A with the needle electrode and the insulation sheath deployed.

Referring to FIG. 5D, as the actuator 66 is pushed down, the stop 76 moves allowing the slide member 69 to move distally until the projection 78 is restrained by a stop 82. The needle electrode 14 is propelled forward as the sliding member 69 is moved by the force from the coiled spring 73. Referring to FIG. 5E, as the slide member 69 moves forward, and just before the end of its distal movement as the projection 78 reaches the stop 82, a trigger member 86 on the slide member 69 contacts a release member 88. Movement of the release member 88 causes the projection 74 to disengage from the stop 76, such that the slide member 68 is propelled forward by the force of the coiled spring 73. As the slide member 68 propels forward, the insulation sheath 40 propels beyond the distal end of the elongated housing 12 covering a pre-determined portion of the needle electrode 14.

Referring to FIG. 5D, in one embodiment, only the needle electrode 14 is propelled with a spring operated actuating mechanism, while the insulation sheath 40 is glided over the needle electrode 14. Once the needle electrode 14 has penetrated the urethral wall, gliding the insulation sheath 40 over the needle electrode 14 can be easily achieved without causing much discomfort to the patient.

In one embodiment, depth of needle electrode 14 penetration is controllable, such that different locations within the prostate can be reached by the needle electrode 14. In one detailed embodiment, the steering mechanism 52 described above can provide depth control. For deeper penetration, the electrode 14 tip can be deflected closer to 90 degrees, whereas for shallow penetration, the needle electrode 14 tip can be deflected by a smaller angle, such as, for example, 45 degrees. In another detailed embodiment, depth of electrode 14 penetration is adjustable using a slide member on the handle 32, which controls movement of the needle electrode 14 relative to the elongated housing 12. In this embodiment, maximum penetration depth may be fixed by placing a stop inside the handle 32.

Figure 6:
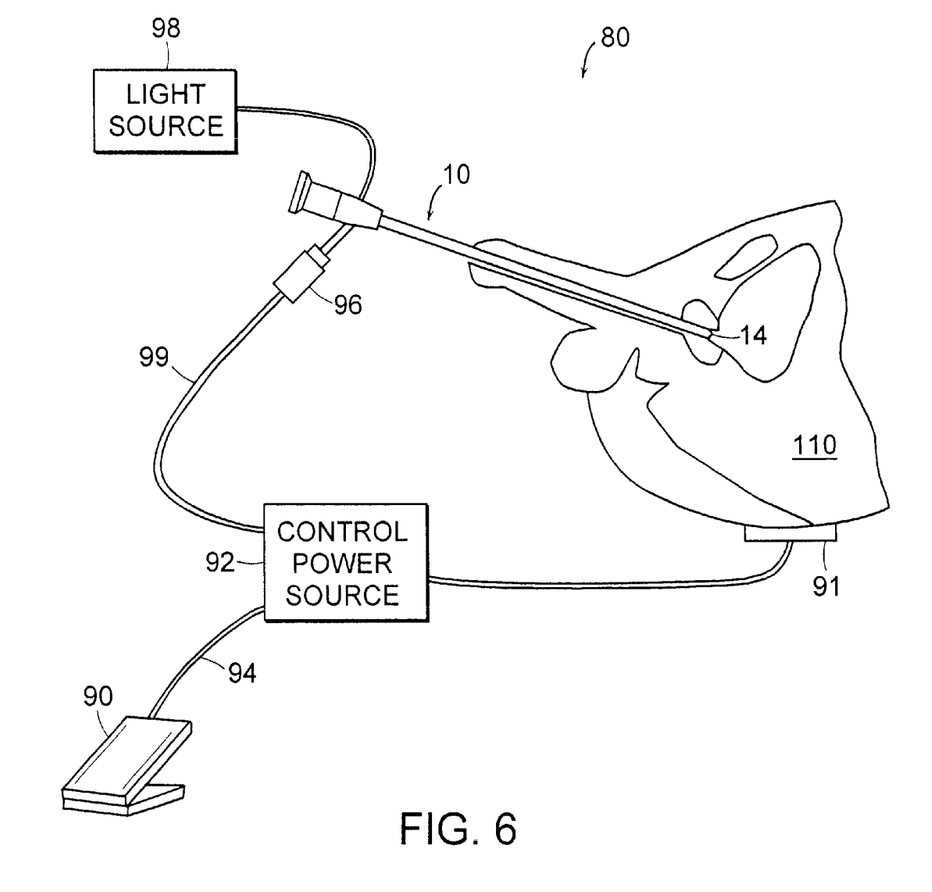
FIG. 6 shows a transurethral interstitial ablation system employing a foot pedal according to one embodiment of the invention.

Referring to FIG. 6, in another embodiment, the electrode 14 can be kinetically deployed using a foot pedal. As shown, the interstitial ablation system 89 includes a foot pedal 90, a control and power source module 92, an actuator, a light source 98, the deflectable interstitial ablation device 10, and a return electrode 91. The light source 98 supplies light to the illumination region 44 of the imaging device 16, described above in FIGS. 3 and 4. As shown in this embodiment, the return electrode 91 is placed on the patient 110. The foot pedal 90 is coupled to the control and power source module via a cable 94, and the control and power source module 92 is coupled to the actuator 96 via a cable 99. In operation, a physician performing an ablation procedure properly places the ablation device 10 inside the patient's body, then steps on the foot pedal 90 to deploy electrode 14, leaving his or her hands free to perform other functions. Additional features such as application of fluid to a treatment site, application of energy to the electrode 14, and the triggering temperature measurement means at the distal end of the electrode 14 may also be activated using the pedal 90. In one embodiment, the interstitial ablation system 89 can include several foot pedal actuators for performing each of these functions. In another embodiment, the interstitial ablation system 89 can include only one foot pedal used to activate multiple functions. In this embodiment, the control module 92 may be programmed to control the order of the performance of each function.

Figure 7:
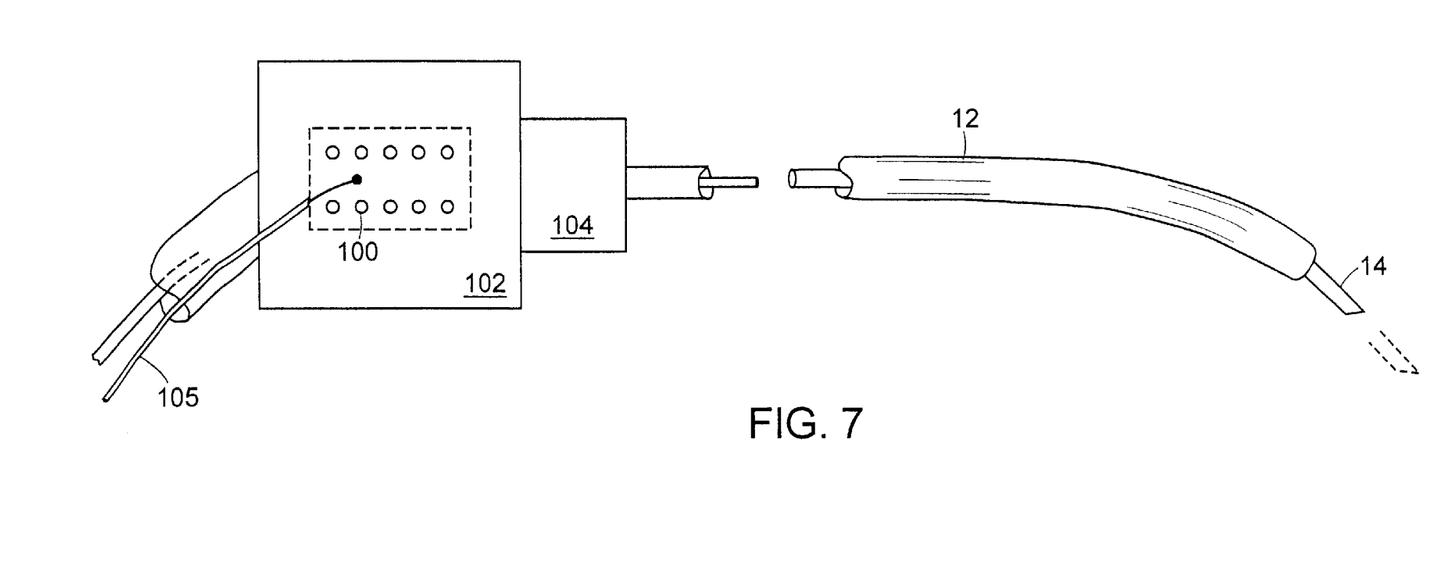
FIG. 7 shows an actuator for deploying a needle electrode according to one embodiment of the invention.

Referring to FIG. 7, shown is the actuator 96 which controls electrode deployment. In the present embodiment, the actuator 96 can comprise a solenoid 100. As shown, the solenoid 100 is coupled to the control and power module 92 at a proximal end via a cable 105, and coupled to the it proximal end of the electrode 14 at a distal end via a luer fitting 104. The actuator 100 is held within an actuator housing 102, which is coupled to the luer fitting 104. The luer fitting 104 is sized and shaped to attach to the proximal end of the elongated housing 12 of the deflectable interstitial ablation device 10. Alternatively, the luer fitting 104 may be sized and shaped to attach to a working channel of a flexible cystoscope for those applications in which cystoscopes are used. When the foot pedal 90 is depressed, current from the power source 92 is applied to the solenoid 100, which forces the electrode 14 to deploy beyond the distal end of the elongated housing 12. Other types of actuators such as a rotary motors and linear motors, as well as other electromechanical devices can be used to perform these functions as well. It is to be appreciated that, a number of foot pedals and actuators for activating a mechanical event can be interchangeably used to actuate the electrode 14, or provide fluid delivery and temperature sensing at the treatment site.

The deflectable interstitial ablation device 10 of the invention provides many other features typically performed in ablation procedures. As briefly described above, the deflectable interstitial ablation device 10 can be coupled to a fluid source to permits delivery of fluid to the housing 12 or to an internal bore (not shown) formed in the electrode 14 such that fluid is dispensed near the treatment site for providing cooling or for enhancing ablation. In such an embodiment, the fluid, can be for example, an electrolytic fluid which increases the ablation area, or a fluid that provides therapeutic effects. In another embodiment, the elongated housing 12 can include a separate passageway suitable for fluid delivery. In both embodiments, fluid can be introduced through the luer port 36 (FIG. 1A). In another embodiment, the solenoid can be coupled to a syringe for introducing fluid inside the elongated housing 12. Application of current to the solenoid in this case would cause the syringe to discharge the fluid held within a fluid source into the elongated housing 12.

In another embodiment, the deflectable interstitial ablation device 10 can include a temperature sensing system for measuring tissue temperature during the ablation procedure. In one detailed embodiment, the temperature sensing system can include a thermocouple disposed near the distal end of the electrode 14, such as by being fixed at the distal end of the insulation sheath 40 that is fixed to the electrode 14. In still another embodiment, the device 10 can include an impedance monitoring system in communication with the proximal end of the electrode 14. The impedance monitoring system can measure impedance near the distal end of the electrode 14. The interstitial ablation device can further employ a feedback system that uses the temperature and or the impedance data to control the delivery of RF energy to the electrode 14. The control module 92 can, for example, include means for automatically adjusting the magnitude and duration of the ablation energy delivered to the electrode in response to one or both of these parameters. The interstitial ablation system can also include a safety feature which cuts off the delivery of energy when the temperature or the impedance value exceeds a threshold value.

The deflectable interstitial ablation device 10 of the present invention does not require the use of an endoscope and therefore can be entirely disposable. The disposable device can attach to reusable eye piece and other equipment such as a light source, and a control and power source module. In an alternative embodiment, the imaging system 16 can be removed from the device 10 for subsequent reuse.

As shown and described, the present invention features an improved transurethral interstitial ablation apparatus and method for performing transurethral ablation. While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A deflectable interstitial ablation device, comprising:
   an elongated housing having a proximal end, a distal end, and a deflectable segment;
   an electrode mounted within the elongated housing and deployable from a first position within the elongated housing to a second position a predetermined distance beyond the distal end of the elongated housing, the electrode having a flexible portion capable of deflecting with the deflectable segment of the elongated housing;
   an imaging device integrally mounted within the elongated housing, the imaging device having a flexible portion capable of deflecting with the deflectable segment of the elongated housing and providing a viewing angle beyond the distal end of the elongated housing, wherein the electrode in the second position remains within the viewing angle and is substantially parallel to a central axis of the viewing angle at any angle of deflection of the electrode;
   a deflection system disposed within the elongated housing for controllably deflecting the deflectable segment of the elongated housing by any angle, the deflection system having a proximal end in communication with a steer mechanism; and
   a foot pedal for remotely activating deployment of the electrode.

2. The deflectable interstitial ablation device of claim 1, wherein the steering mechanism is handle-operable.

3. The deflectable interstitial ablation device of claim 1, wherein the foot pedal is further adapted for activating a temperature sensor disposed near a distal end of the electrode.

4. The deflectable interstitial ablation device of claim 1, wherein the deflectable segment is disposed at the distal end of the elongated housing.

5. A deflectable interstitial ablation device, comprising:
   an elongated housing comprising a proximal end, a distal end, and a deflectable segment;
   an electrode mounted within the elongated housing, the electrode deployable from a first position within the elongated housing to a second position a predetermined distance beyond the distal end of the elongated housing and in communication with a radio frequency generator;
   a temperature sensing system in communication with a distal end of the electrode for measuring a temperature;
   a feedback system using data generated from the temperature sensing system for controlling the delivery of radio frequency energy to the electrode;
   an imaging device integrally mounted within the elongated housing, the imaging device comprising a flexible portion capable of deflecting with the deflectable segment of the elongated housing and providing a viewing angle beyond the distal end of the elongated housing, wherein the electrode in the second position remains within the viewing angle and is substantially parallel to a central axis of the viewing angle at any angle of deflection of the electrode; and
   a deflection system disposed within the elongated housing for controllably deflecting the deflectable segment of the elongated housing by any angle, the deflection system comprising a proximal end in communication with a steering mechanism.

6. The deflectable interstitial ablation device of claim 5, wherein the steering mechanism is handle-operable.

7. The deflectable interstitial ablation device of claim 5, further comprising a impedance monitoring system in communication with a proximal end of the electrode for measuring an impedance.

8. The deflectable interstitial ablation device of claim 7, further comprising a feedback system that uses data generated from the impedance monitoring system for controlling the delivery of radio frequency energy to the electrode.

9. The deflectable interstitial ablation device of claim 7, further comprising a safety feature which cuts off delivery of radio frequency energy to the electrode when temperature or impedance exceed a threshold value.

10. The deflectable ablation device of claim 5, further comprising a safety feature which cuts off delivery of radio frequency energy to the electrode when the temperature exceeds a threshold value.

11. A deflectable interstitial ablation device, comprising:
   an elongated housing comprising a proximal end, a distal end, and a deflectable segment;
   an electrode mounted within the elongated housing, the electrode deployable from a first position within the elongated housing to a second position a predetermined distance beyond the distal end of the elongated housing and in communication with a radio frequency generator;
   an impedance monitoring system in communication with the electrode for measuring an impedance;
   a feedback system using data generated from the impedance monitoring system for controlling the delivery of radio frequency energy to the electrode;
   an imaging device integrally mounted within the elongated housing, the imaging device comprising a flexible portion capable of deflecting with the deflectable segment of the elongated housing and providing a viewing angle beyond the distal end of the elongated housing, wherein the electrode in the second position remains within the viewing angle and is substantially parallel to a central axis of the viewing angle at any angle of deflection of the electrode; and
   a deflection system disposed within the elongated housing for controllably deflecting the deflectable segment of the elongated housing by any angle, the deflection system comprising a proximal end in communication with a steering mechanism.

12. The deflectable interstitial ablation device of claim 11, wherein the steering mechanism is handle-operable.

13. The deflectable interstitial ablation device of claim 11, further comprising a temperature sensing system for measuring a temperature.

14. The deflectable interstitial ablation device of claim 13, further comprising a feedback system that uses data generated from the temperature sensing system for controlling the delivery of radio frequency energy to the electrode.

15. The deflectable interstitial ablation device of claim 11, further comprising a safety feature which cuts off delivery of radio frequency energy to the electrode when impedance exceeds a threshold value.

16. The deflectable interstitial ablation device of claims 13, further comprising a safety feature which cuts off delivery of radio frequency energy to the electrode when temperature or impedance exceed a threshold value.

17. A deflectable interstitial ablation device, comprising:
   an elongated housing comprising a proximal end, a distal end, and a deflectable segment,
   a basket disposed along a length of the elongated housing, the basket adapted for maintaining the placement of the device in a body umen;
   an electrode mounted within the elongated housing and deployable from a first position within the elongated housing to a second position a predetermined distance beyond the distal end of the elongated housing, the electrode comprising a flexible portion capable of deflecting with the deflectable segment of the elongated housing;
   an imaging device integrally mounted within the elongated housing, the imaging device comprising a flexible portion capable of deflecting with the deflectable segment of the elongated housing;
   a deflection system, disposed within the elongated housing for controllably deflecting the deflectable segment of the elongated housing by any angle, the deflection system comprising a proximal end in communication with a steering mechanism; and
   a driver for deploying the electrode from the first position to the second position.

18. The deflectable interstitial ablation device of claim 17, wherein the basket comprises a wire mesh attached to an outer surface of the housing.

* * * * *

UNITED STATES PATENT AND TRADEMARK OFFICE
CERTIFICATE OF CORRECTION

PATENT NO.     : 6,482,203 B2
DATED          : November 19, 2002
INVENTOR(S)    : Paddock et al.

It is certified that error appears in the above-identified patent and that said Letters Patent is hereby corrected as shown below:

<u>Title page,</u>
Item [54], Title, delete "DELECTABLE", insert -- DEFLECTABLE --.

Signed and Sealed this

Eighteenth Day of February, 2003

JAMES E. ROGAN
*Director of the United States Patent and Trademark Office*